(12) United States Patent
Rouse et al.

(10) Patent No.: US 10,765,536 B2
(45) Date of Patent: Sep. 8, 2020

(54) CATAPULT ANKLE AND RELATED METHODS

(71) Applicant: Rehabilitation Institute of Chicago, Chicago, IL (US)

(72) Inventors: Elliot Rouse, Chicago, IL (US); Pooya Heiraty, La Grange Park, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 0 days.

(21) Appl. No.: 15/294,614

(22) Filed: Oct. 14, 2016

(65) Prior Publication Data

US 2017/0105851 A1 Apr. 20, 2017

Related U.S. Application Data

(60) Provisional application No. 62/241,489, filed on Oct. 14, 2015.

(51) Int. Cl.
| | |
|---|---|
| A61F 2/66 | (2006.01) |
| A61F 2/50 | (2006.01) |
| A61F 2/70 | (2006.01) |
| A61F 2/76 | (2006.01) |
| A61F 2/68 | (2006.01) |

(52) U.S. Cl.
CPC .... *A61F 2/6607* (2013.01); *A61F 2002/5072* (2013.01); *A61F 2002/6845* (2013.01); *A61F 2002/701* (2013.01); *A61F 2002/704* (2013.01); *A61F 2002/7615* (2013.01); *A61F 2002/7625* (2013.01); *A61F 2002/7635* (2013.01)

(58) Field of Classification Search
CPC .................. A61F 2/6607; A61F 2002/5072
See application file for complete search history.

(56) References Cited

U.S. PATENT DOCUMENTS

| | | | | |
|---|---|---|---|---|
| 8,480,760 B2* | 7/2013 | Hansen | ................. | A61F 2/6607 623/47 |
| 8,734,528 B2* | 5/2014 | Herr | ......................... | A61F 2/60 623/24 |
| 9,289,316 B2* | 3/2016 | Ward | .................... | A61F 2/6607 |
| 2006/0249315 A1* | 11/2006 | Herr | ......................... | A61F 2/60 180/8.1 |
| 2014/0330393 A1* | 11/2014 | Ward | .................... | A61F 2/6607 623/24 |

* cited by examiner

*Primary Examiner* — Bruce E Snow
*Assistant Examiner* — Melissa A Hoban
(74) *Attorney, Agent, or Firm* — McAndrews, Held & Malloy, Ltd.

(57) ABSTRACT

Catapult ankles and related methods are disclosed. An example ankle prosthesis for operation in a swing phase and in a stance phase includes a motor, wherein the motor is configured to store energy with a first spring during the swing phase and plantarflex the ankle prosthesis during a push off portion of the stance phase.

16 Claims, 5 Drawing Sheets

CATAPULT ANKLE AND RELATED METHODS

RELATED APPLICATIONS

This patent claims priority to U.S. Provisional Patent Application Ser. No. 62/241,489, filed on Oct. 14, 2015, entitled "Catapult Ankle and Related Methods." The entirety of U.S. Provisional Patent Application Ser. No. 62/241,489 is incorporated herein by reference.

FEDERALLY SPONSORED RESEARCH OR DEVELOPMENT

[Not Applicable]

MICROFICHE/COPYRIGHT REFERENCE

[Not Applicable]

BACKGROUND

Lower limb loss causes severe mobility deficits that affect many other aspects of lives of amputees, including decreased community involvement and depression. One major cause for these mobility challenges is the lack of small, lightweight leg prostheses that can provide power like the human neuromuscular system. A person's walking or other ambulation gait can be cyclical, with a stance phase and a swing phase. Stance phase is the part of the gait cycle when weight is borne by the leg. Swing phase is the part of the gait cycle when the foot is in the air and weight is borne by the opposite leg.

The human ankle is important for walking because it provides over half of the energy required to move the body forward. The ankle produces energy during part of the gait cycle known as "push off" or "powered plantarflexion." During push off, the calf muscle contracts and propels the body into the next step. During the remainder of the gait cycle, the ankle produces little to no power.

COMPONENT LIST 5 ankle system
10 motor
20 transmission
21 gear stage one
22 gear
23 gear stage 2
24 gear
25 output from gear 24
26 charging disk
27 chassis
28 spring pegs on the charging disk
29 spring pegs on the chassis
50 springs latex springs between each of 28 and 29
30 bearing blocks
31 gas spring. One end connected to chassis 27, other end connected to foot 32
32 foot
33 ankle axle (ankle joint)
34 clutch.
35 microcontroller
36 clutch motor
37 sensor
38 sensor
40 axle

DETAILED DESCRIPTION

In an embodiment, an ankle system stores energy in a spring or a plurality of springs over a longer duration than just the period of push-off (in one example, for the entire gait cycle), and releases the energy when needed (in one example, push off). This design permits the use of a small, low power motor, instead of a heavier high power motor. The substantially reduced weight may ease the burden for amputees wearing a robotic ankle. The robotic ankle may be manufactured using the design described herein, and its control may be implemented on a microcontroller programmed with a finite state machine or another algorithm. In an embodiment, the ankle system uses a catapult mechanism to propel the ankle system forward during plantarflexion.

Figure 1:
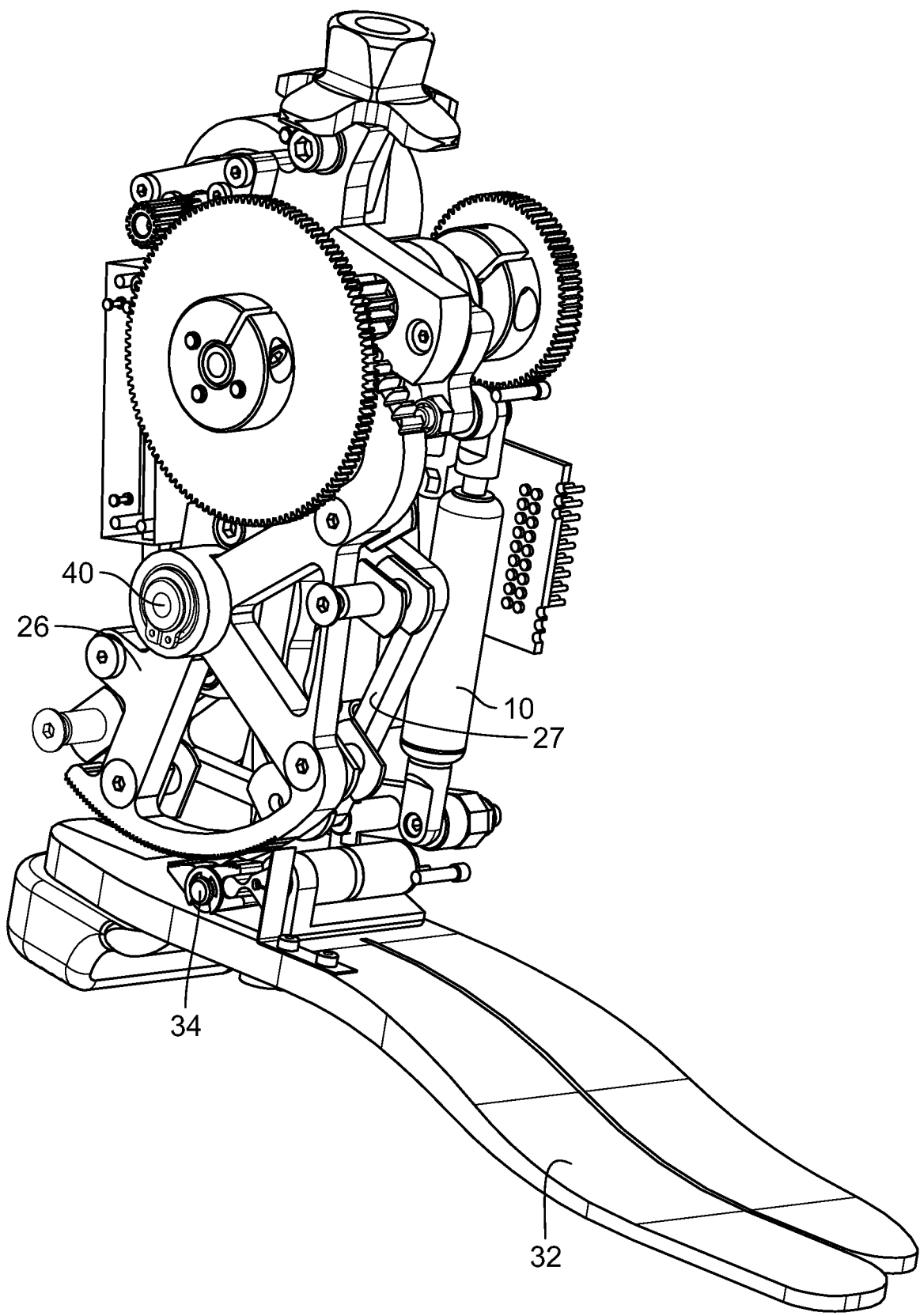
FIG. 1 is a profile view of a prosthetic ankle system.
Figure 2:
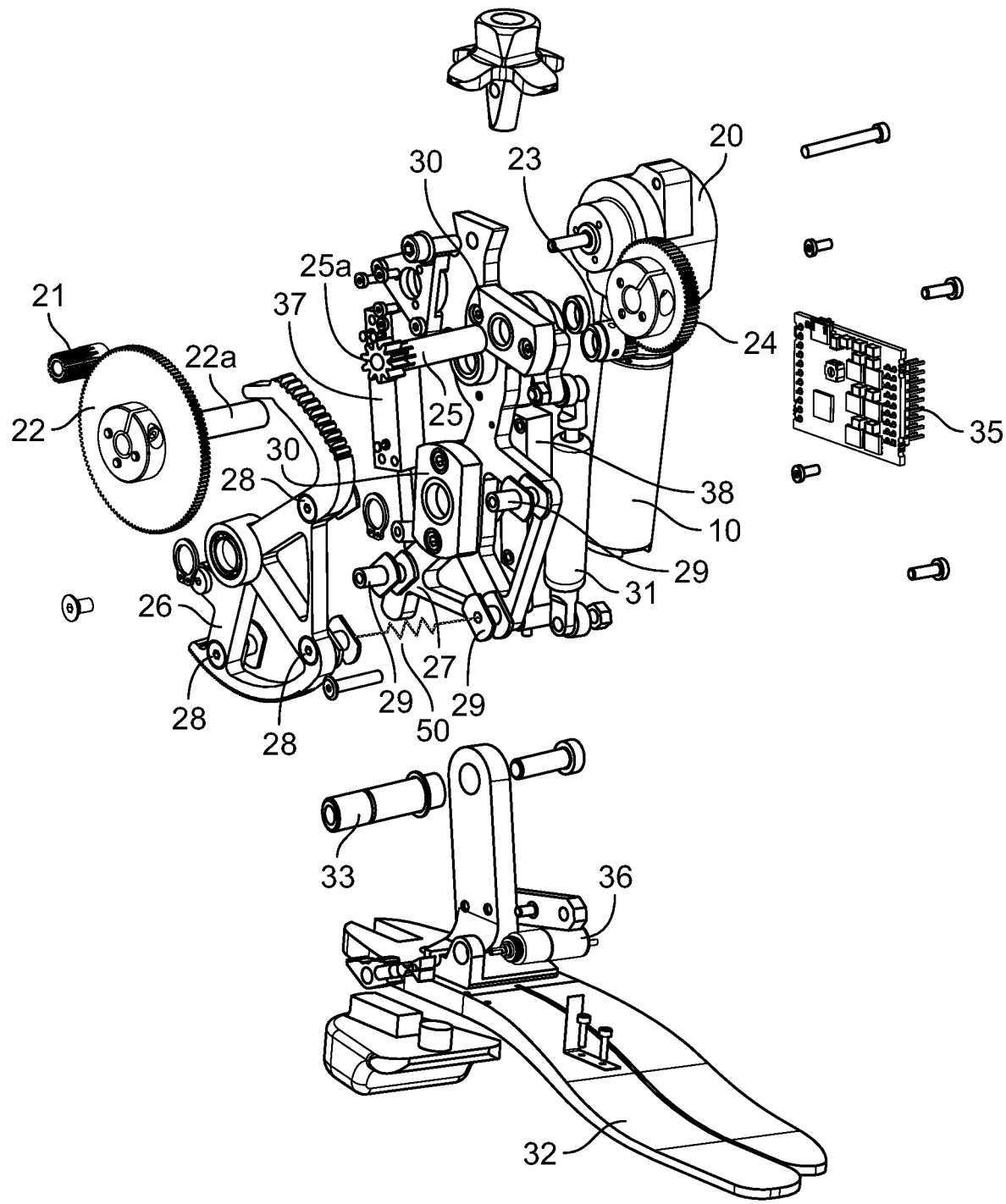
FIG. 2 is an exploded view of the prosthetic ankle system shown in FIG. 1.

FIGS. 1 and 2 illustrate a profile view and an exploded view, respectively, of an embodiment of ankle system 5. The ankle system 5 comprises a motor 10, a charging disk 26, a chassis 27, springs 50, spring 31, a clutch 34, and a foot 32. As illustrated in FIG. 2, the springs 50 are connected between the charging disk 26 and the chassis 27. The motor 10 may run throughout all of the gait cycle, in order to provide the most power available to the ankle system 5 during powered plantarflexion.

During stance phase before push-off, the ankle system 5 stores energy in the spring 31. During swing phase, the motor operates to store energy in the ankle system 5 in both the stance and swing springs. During push off of the ankle system 5, the energy stored the ankle system is released. For example, a spring system may store energy in the ankle system 5 until it is released during push-off. The clutch may be used to disengage the motor 10 from the ankle joint while energy is stored in the spring 31. The motor and springs may be selected based on their ability to facilitate the appropriate mechanical power and energy storage.

During the swing phase and the stance phase from toe-strike to mid-stance, the motor 10 runs to store energy in one or more of the springs 50 and the spring 31. Energy in the springs 50 is stored by the charging disk 26 rotating about an axle 40 in relation to the chassis 27, which is fixed. Energy in the spring 21 is stored when dorsiflexion of the foot 32 caused by running of the motor 10 and the ground reaction forces created when the foot 32 strikes the ground causes the spring 21 to compress. During powered plantarflexion, the motor 10 reverses its operation, and the energy from the motor 10, the springs 50, and the spring 31 all operate in the same direction to provide an increased torque to assist the user plantarflex the ankle system 5.

As illustrated in FIGS. 1 and 2, the motor 10 is coupled to a transmission 20, which turns a first gear stage and a second gear stage. The first gear stage comprises gear 21 and gear 22, where the rotation of gear 21 causes an opposite rotation of gear 22. The gear 22 has a link 22a attached at the center of the gear 22 and extending therefrom. The link 22a connects to gear 23 (also illustrated in FIG. 6, a side view of the catapult ankle system). The second gear stage comprises gear 23, gear 24, and output member 25, where rotation of gear 23 causes an opposite rotation of gear 24. Gear 24 is connected to output member 25, which may be positioned through bearing block 30. Output member 25 has a sprocket 25a that interfaces with the teeth of the charging disk 26, so that rotation of the output member 25 causes the charging disk 26 to rotate about the axle 40. In the embodiment shown in FIG. 2, sensor 37 and sensor 38 may be used to determine the position of each of the gas spring 31, chassis 27, charging disk 26, ankle axle 33, and clutch 34. As illustrated in FIG. 2, the gas spring 31 may be connected, on one end, to chassis 27, and on the other end, to foot 32.

Figure 4:
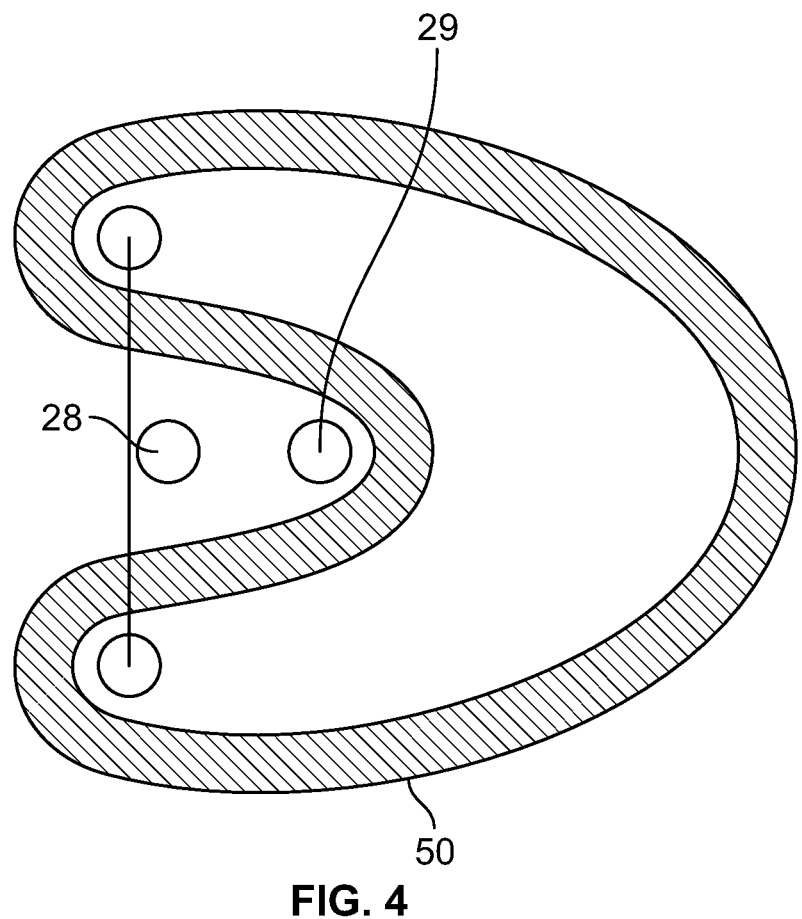
FIG. 4 is a profile view of spring held in place by spring pegs for use in the prosthetic ankle system shown in FIG. 1

Spring pegs 28 attached to the charging disk 26 and spring pegs 29 attached to the chassis 27 hold the springs 30 in place. Springs 50 may be latex springs. In an embodiment, each spring 50 is a circular latex spring. FIG. 4 shows a side profile illustration of an embodiment of a spring 50 held in place by spring pegs 28 and 29.

Figure 5:
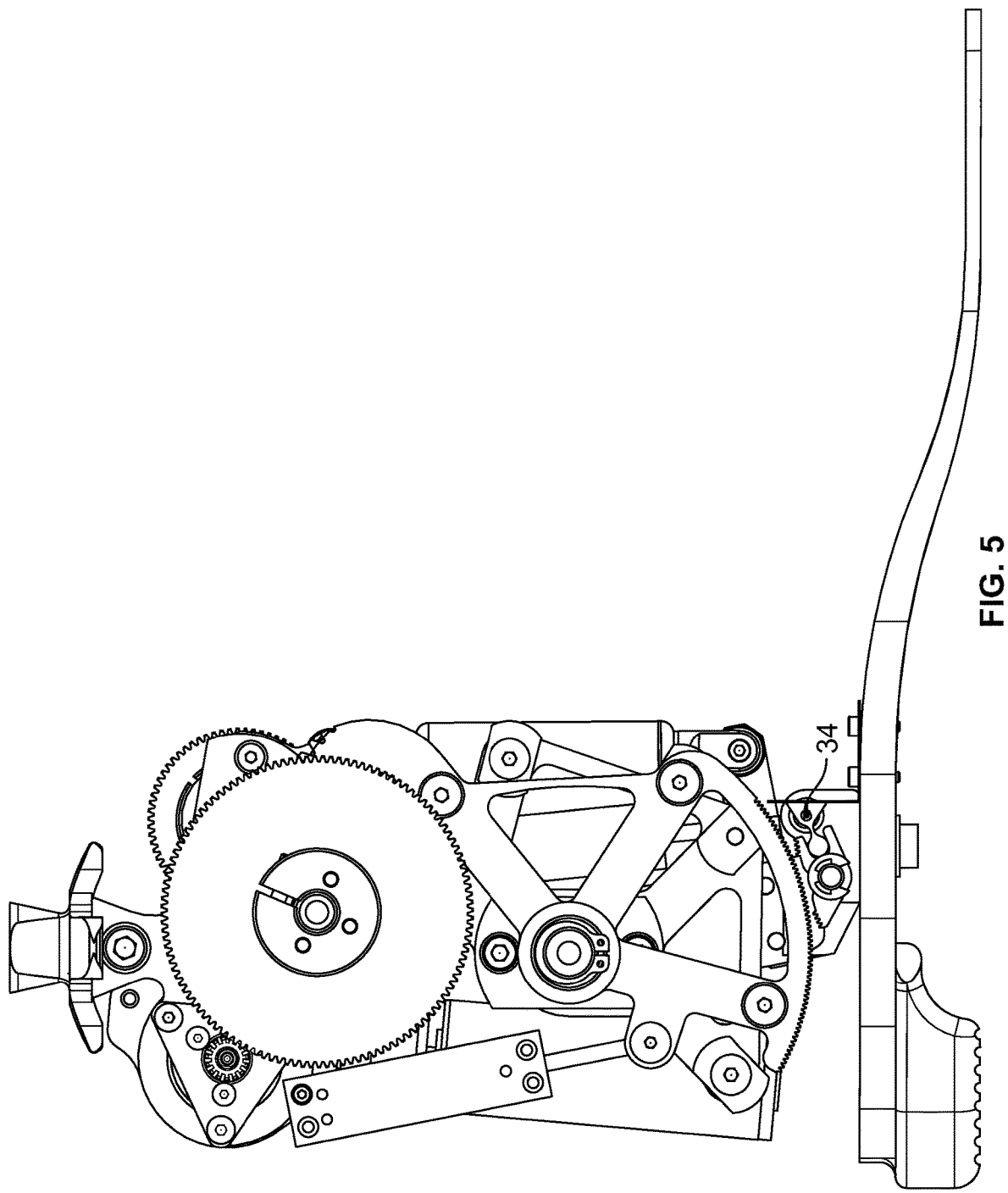
FIG. 5 is a side view of the prosthetic ankle system shown in FIG. 1.
Figure 6:
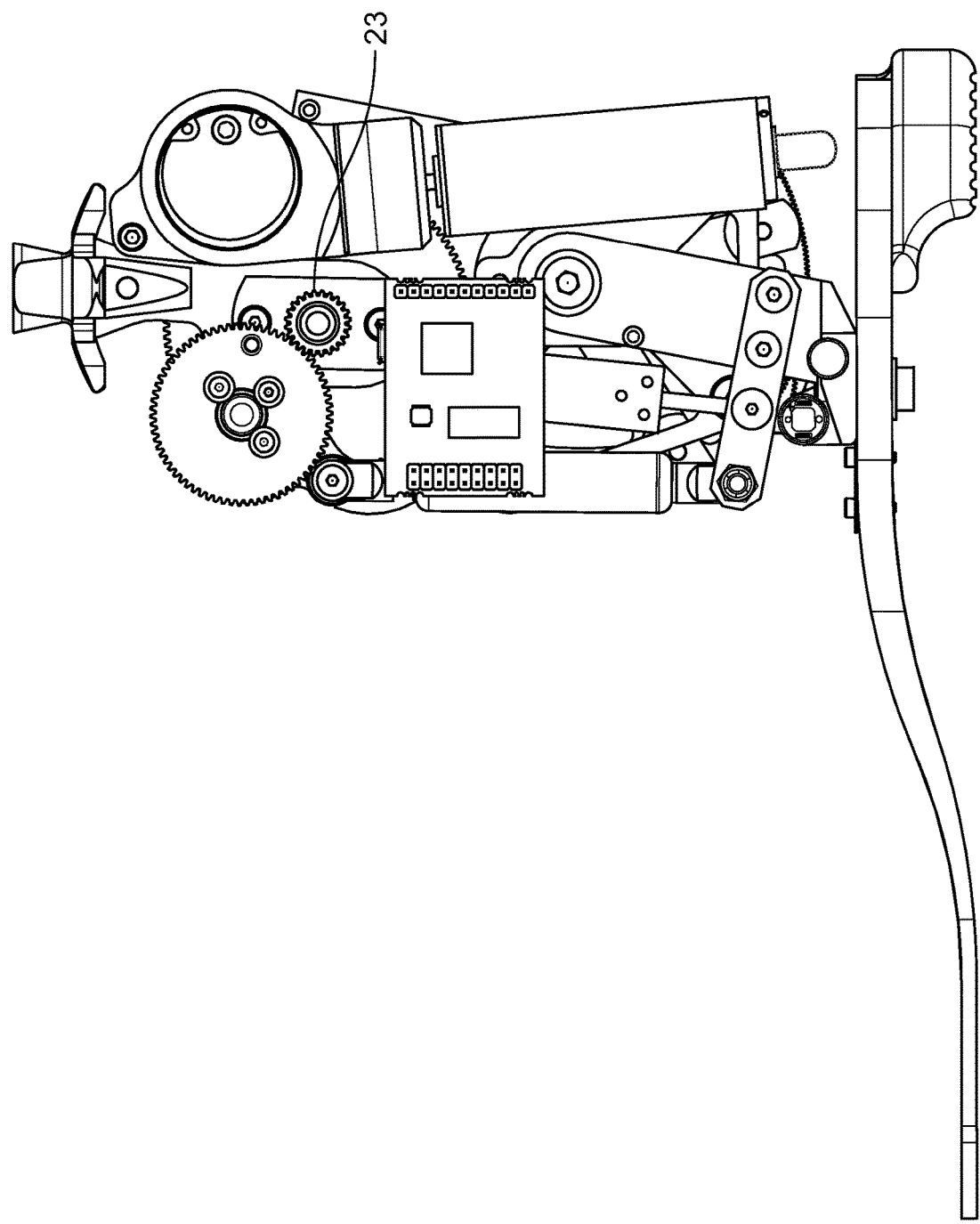
FIG. 6 is a side view of the prosthetic ankle system shown in FIG. 1.

Various clutch configurations may be used in various embodiments of an ankle system. As illustrated in FIGS. 5 and 6, side views of the catapult ankle system, in an embodiment, the clutch 34 may be shaped so that when the clutch 34 is adjusted upwards towards the ankle system 5, the teeth of the clutch 34 engage against the charging disk 26 to prevent the charging disk from rotating in a first direction. When the clutch is adjusted upwards towards the ankle system 5 in the opposite direction, the teeth of the clutch 34 engage against the charging disk 26 to prevent the charging disk 26 from rotating in a direction opposite the first direction. The clutch 34 may have its own motor, which may be coupled to an actuator to move the clutch 34 upwards towards the ankle system.

During the swing phase of the ankle system 5, the clutch 34 is engaged and the foot is dorsiflexed, which causes energy to be stored in spring 31 and springs 50. During the early to mid-stance phase of the ankle system 5, the clutch 34 disengages when the user's own ground reaction opposes the spring 31 and springs 50. Once the clutch 34 has disengaged, the motor 10 stores energy in the springs 50, and the user's force on the ankle system 5 stores energy in the spring 31. At push off of the ankle system 5, the clutch 34 engages again, and the motor 10, the springs 50, and the spring 31 operate together to provide energy in the same direction to assist in plantarflexion. The clutch 34 is only not engaged between early/mid-stance and push off. In the ankle system 5, energy is stored in the springs 50 when the charging disk 26 rotates in a first direction with respect to the chassis 27, which stretches the springs 50.

Motor 10 may be a brushless motor operated by a controller 35. In an embodiment, the controller 35 may control the motor 10 and also may control the motor of the clutch 34. The controller 35 may be coupled to sensors 37 and 38 (which may be linear potentiometers) attached to the ankle system 5, which can detect the kinematics of the ankle system 5. The controller 35, the sensors, and the clutch 34 may be coupled together using appropriate communication busses, other electronics (such as FET switches) and power sources (such as a 12V LiPo battery).

In an embodiment, the controller 35 determines that the ankle system 5 is in swing phase by using information from the sensors to determine the angle threshold of the ankle system 5, which indicates whether the ankle is plantarflexed. The controller 35 sends an instruction to the motor 10 to dorsiflex the foot 32 to a sufficient dorsiflexion angle at the start of swing. The controller 35 then waits to receive information from the sensors that indicate start of stance (for instance, by an identification of heel contact). As the user begins to put his or her body weight on the ankle system 5, the weight of the user counteracts the other torque on the clutch 34 and the clutch disengages. As the ankle system 5 transitions from mid-phase, the ankle system 5 rolls over, then stops from rolling over just before plantarflexion. The ankle speed just before plantarflexion is equal to 0. The sensors indicate to the controller 35 that the ankle speed is equal to 0, causing the controller 35 to cause the clutch 34 to engage, causing the motor 10, the springs 50, and the gas spring 31 to release their energy to plantarflex the ankle system 5.

The controller may be programmed with a control system based on a finite state control system architecture. This architecture employs a set of concatenated states with specific mechanical behaviors. During operation, the machine cycles through the states, which provide the behavior needed for walking. There are two parts to the finite state machine—the state behaviors and the state transitions. Based on the desired operation of the ankle, there may be four states.

Figure 3:
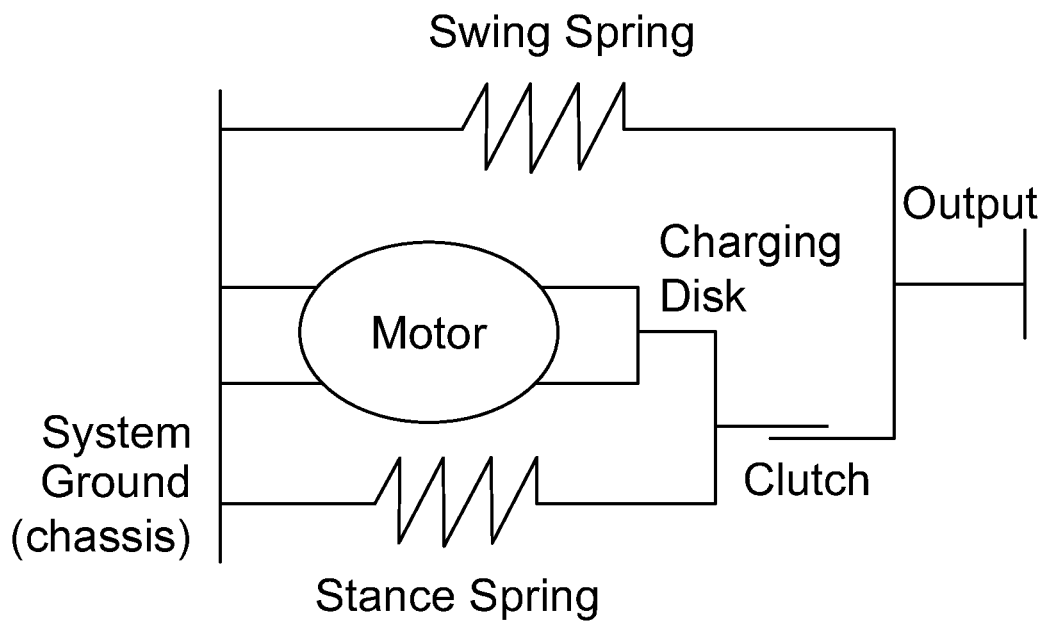
FIG. 3 is a diagram illustrating the general positioning of the elements of the prosthetic ankle system shown in FIG. 1

FIG. 3 illustrates a diagram that shows the general positioning of elements of an embodiment of an ankle system. One possible use of the ankle system is briefly described. During swing phase, the motor stores energy in both the stance and swing springs by compressing the stance spring and the swing spring towards system ground. During the early to mid-stance phase, the clutch disengages and the motor stores energy in the stance spring and the user's force on the system stores energy in the swing spring. At push off of the ankle system, the clutch engages and the motor, the stance spring, and the swing spring operate so that the energy stored in both springs is released to the wearer with high power. The clutch is used to disengage the motor from the ankle joint while energy is stored in the stance spring. The motor and springs may be selected based on their ability to facilitate the appropriate mechanical power and energy storage.

What is claimed is:

1. An ankle prosthesis for operation in a swing phase and in a stance phase, comprising:
   a motor, wherein the motor is configured to:
      store energy with a first spring during the swing phase; and
      plantarflex the ankle prosthesis during a push off portion of the stance phase;
   one or more sensors; and
   a controller configured to:
      determine whether the ankle prosthesis is in the swing phase or the stance phase based on information from the one or more sensors;
      control the motor to dorsiflex the ankle prosthesis based on a start of the swing phase; and
      control a clutch coupled to the motor to engage during the push off portion of the stance phase, to thereby cause the motor to plantarflex the ankle prosthesis in cooperation with the first spring during the push off portion of the stance phase;
   wherein the first spring is configured to store energy in a charging disk during the swing phase, and to release the stored energy from the charging disk to plantarflex the ankle prosthesis during the push off portion of the stance phase.

2. The ankle prosthesis of claim 1, wherein the motor operates
   in a first direction while storing energy with the first spring during the swing phase; and
   in a second direction opposite the first direction while plantarflexing the ankle prosthesis during push off.

3. The ankle prosthesis of claim 1, further comprising a second spring positioned to store energy when the ankle prosthesis is dorsiflexed and to release the energy stored with the second spring to plantarflex the ankle prosthesis during the push off portion of the stance phase.

4. The ankle prosthesis of claim 3, wherein the clutch is configured to:
   a. engage during the swing phase to store energy from the motor with the first spring and the second spring;
   b. disengage during the early to mid-phase to store energy from the motor with the first spring and to permit dorsiflexion of the ankle prosthesis to store energy with the second spring; and
   c. engage to provide energy from the motor, the first spring, and the second spring to plantarflex the ankle prosthesis at push off.

5. The ankle prosthesis of claim 4, wherein the clutch is configured to disengage in response to a force placed onto the ankle prosthesis by a user of the ankle prosthesis.

6. The ankle prosthesis of claim 4, wherein the clutch is configured to engage in response to an ankle speed of the ankle prosthesis.

7. The ankle prosthesis of claim 4, wherein the first spring is attached to a charging disk and stores energy from the motor in the charging disk.

8. The ankle prosthesis of claim 7, wherein the clutch is configured to engage with the charging disk.

9. The ankle prosthesis of claim 1, wherein the clutch is positioned between the motor and a chassis of the ankle prosthesis, wherein the clutch is engageable to allow the energy stored with the first spring to plantarflex the ankle prosthesis during push off.

10. The ankle prosthesis of claim 9, wherein the clutch is moved from a disengaged position to an engaged position in an early to mid-phase of the stance phase.

11. The ankle prosthesis of claim 1, wherein the clutch is positioned between the motor and a chassis of the ankle prosthesis, wherein the clutch is engageable to allow the motor to plantarflex the ankle prosthesis during push off.

12. The ankle prosthesis of claim 11, wherein the clutch is moved from a disengaged position to an engaged position in an early to mid-phase of the stance phase.

13. The ankle prosthesis of claim 1, wherein the motor is further configured to operate during all of the swing phase.

14. The ankle prosthesis of claim 13, wherein the motor is further configured to operate during all of the stance phase.

15. An ankle prosthesis for operation in a swing phase and in a stance phase, comprising:
   a chassis;
   a first spring coupled to the chassis and configured to store energy in a charging disk during the swing phase and release the stored energy from the charging disk to plantarflex the ankle prosthesis during a push off portion of the stance phase;
   a motor coupled to the chassis and configured to:
      store energy in the first spring during the swing phase; and
      in cooperation with the first spring, plantarflex the ankle prosthesis during the push off portion of the stance phase;
   a clutch configured to:
      selectively decouple the motor and the first spring from an ankle joint to cause the motor to store the energy in the first spring; and
      selectively couple the motor and the first spring to the ankle joint to cause the motor and the first spring to plantarflex the ankle prosthesis;
   one or more sensors; and
   a controller configured to:
      determine whether the ankle prosthesis is in the swing phase or the stance phase based on information from the one or more sensors; and
      control the clutch to couple the motor and the first spring to the ankle joint to cause the motor and the first spring to plantarflex the ankle prosthesis during the push off portion of the stance phase.

16. The ankle prosthesis of claim 15, further comprising:
   a foot; and
   a second spring configured to:
      store energy via the foot between an early-stance portion a mid-stance portion of the stance phase; and
      release the stored energy in the second spring to, in cooperation with the motor and the first spring, plantarflex the ankle prosthesis during the push off portion of the stance phase.

* * * * *